United States Patent [19]

Kusleika

[11] Patent Number: 5,722,979
[45] Date of Patent: Mar. 3, 1998

[54] PRESSURE ASSISTED ULTRASONIC BALLOON CATHETER AND METHOD OF USING SAME

[75] Inventor: Richard S. Kusleika, Eden Prairie, Minn.

[73] Assignee: Schneider (USA) Inc., Plymouth, Minn.

[21] Appl. No.: 826,889

[22] Filed: Apr. 8, 1997

[51] Int. Cl.⁶ .................................................. A61M 25/10
[52] U.S. Cl. .......................... 606/108; 606/169; 606/194; 604/22
[58] Field of Search ............................ 604/22; 606/108, 606/159, 169, 194

[56] References Cited

U.S. PATENT DOCUMENTS

| | | | |
|---|---|---|---|
| D. 363,777 | 10/1995 | Rees | D24/146 |
| 3,994,294 | 11/1976 | Knute | 128/214 F |
| 4,439,186 | 3/1984 | Kuhl | 604/99 |
| 4,446,867 | 5/1984 | Leveen et al. | 128/344 |
| 4,493,697 | 1/1985 | Krause et al. | 604/50 |
| 4,655,771 | 4/1987 | Wallsten | 623/1 |
| 4,733,665 | 3/1988 | Palmaz | 128/343 |
| 4,762,129 | 8/1988 | Bonzel | 128/344 |
| 4,872,483 | 10/1989 | Shah | 137/557 |
| 5,002,531 | 3/1991 | Bonzel | 604/96 |
| 5,152,776 | 10/1992 | Pinchuk | 606/192 |
| 5,163,421 | 11/1992 | Bernstein et al. | 128/24.1 |
| 5,232,445 | 8/1993 | Bonzel | 604/96 |
| 5,269,291 | 12/1993 | Carter | 128/24 |
| 5,269,297 | 12/1993 | Weng et al. | 128/24 |
| 5,380,273 | 1/1995 | Dubrul et al. | 604/22 |
| 5,382,228 | 1/1995 | Nita et al. | 604/22 |
| 5,409,495 | 4/1995 | Osborn | 606/108 |
| 5,417,672 | 5/1995 | Nita et al. | 604/283 |
| 5,423,759 | 6/1995 | Campbell | 604/153 |
| 5,427,118 | 6/1995 | Nita et al. | 128/772 |
| 5,447,509 | 9/1995 | Mills et al. | 606/1 |
| 5,451,220 | 9/1995 | Ciervo | 606/1 |
| 5,460,609 | 10/1995 | O'Donnell | 604/100 |
| 5,472,406 | 12/1995 | de la Torre et al. | 601/2 |
| 5,474,530 | 12/1995 | Passafaro et al. | 604/22 |
| 5,498,236 | 3/1996 | Dubrul et al. | 604/22 |
| 5,524,620 | 6/1996 | Rosenchein | 128/653.1 |
| 5,611,807 | 3/1997 | O'Boyle | 606/169 |

FOREIGN PATENT DOCUMENTS

| | | |
|---|---|---|
| 0276535A1 | 8/1988 | European Pat. Off. . |
| 0363203A3 | 4/1990 | European Pat. Off. . |
| 2533315A1 | 9/1976 | Germany . |
| 3538739A1 | 5/1987 | Germany . |
| 523074 | 5/1972 | Switzerland . |

OTHER PUBLICATIONS

Effect of Low Frequency Vibration on the Arterial Wall, by Derek R. Boughner and Margo R. Roach, Circulation Research, vol. XXIX, Aug. 1971.

*Primary Examiner*—Michael Buiz
*Assistant Examiner*—David O. Reip
*Attorney, Agent, or Firm*—Peter C. Richardson; Lawrence C. Akers; Philip C. Strassburger

[57] ABSTRACT

An ultrasonic balloon catheter and stent assembly including ultrasonic acoustical oscillating energy for low pressure balloon inflation and expansion of implantable devices including stents. The ultrasonic balloon catheter may also be used in low pressure angioplasty procedures.

22 Claims, 3 Drawing Sheets

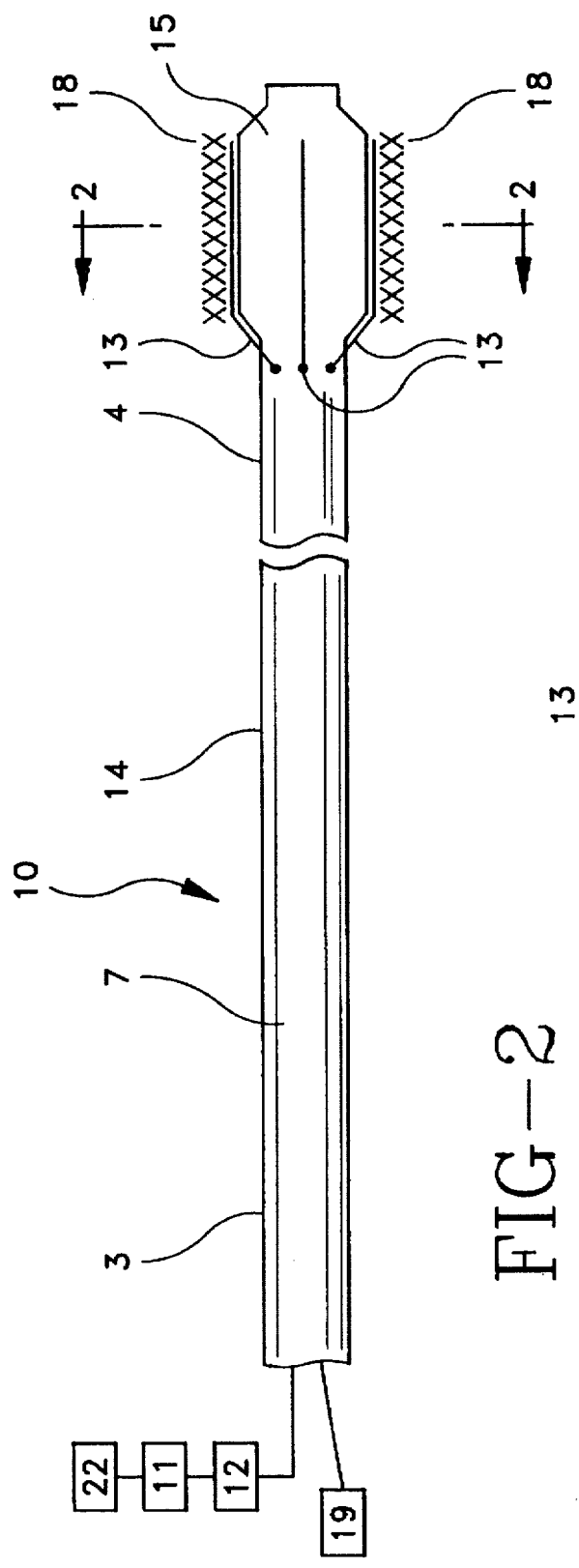

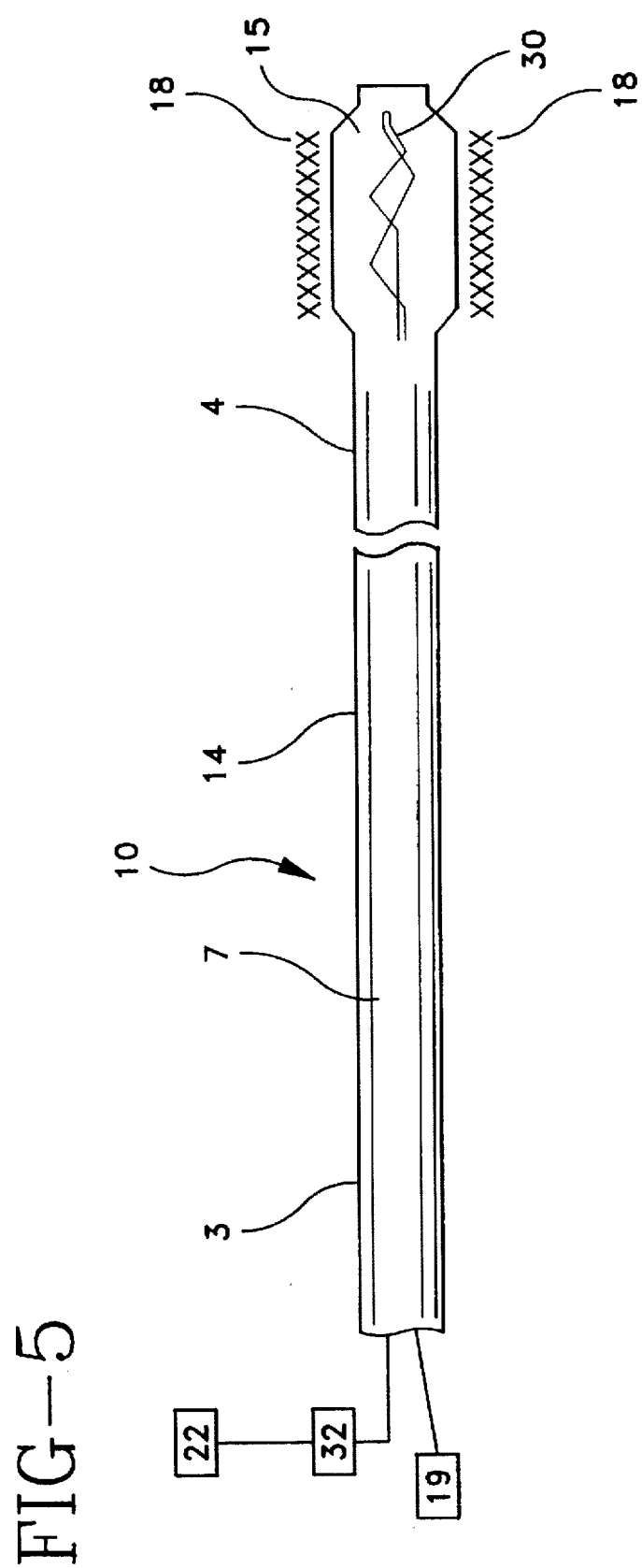

PRESSURE ASSISTED ULTRASONIC BALLOON CATHETER AND METHOD OF USING SAME

BACKGROUND OF THE INVENTION

This invention relates to dilatation catheters and more particularly to dilatation catheters adapted for low pressure stent dilatation and angioplasty.

Balloon catheters are used in percutaneous transluminal coronary angioplasty, stent dilatation, and in other medical procedures to repair arteries and maintain blood flow through the body lumens.

Early research found that a rigorous and prolonged anticoagulation regimen may be required following stent implantation into a coronary artery. Often, if anticoagulation therapy was not used, the stents thrombosed. More recent research has attributed thrombolysis, in some cases, to stents not being fully apposed to the arterial walls. Intravascular ultrasound has shown that the typical 12–14 atm of pressure used to deploy rigid metal stents does not always uniformly cause the stent to fully appose and be in close contact with the arterial walls.

It has been demonstrated that high pressure balloon angioplasty, using a high pressure noncompliant balloon at typically 20 atm of pressure inside a deployed stent may cause good stent and arterial wall apposition and may reduce or eliminate patient anticoagulation regimens following stent implantation. However, high pressure may have certain disadvantages. For example, if the balloon ruptures, medical complications may result. Also, if a balloon is not accurately placed and extends from the stent, relatively healthy artery may be damaged by the relatively higher pressure inflation.

Low pressure dilatation of stents and balloon angioplasty offers an advantage in that potential medical complications are minimized and reduced.

The need for low pressure dilatation of stents and balloon angioplasty has particularly become more important with advances in micro-surgery, neuro-surgery, and conventional angioplasty procedures.

Various catheters are known in the art including U.S. Pat. Nos. B14,762,129; 5,002,531; and 5,232,445. Various stents are known in the art including U.S. Pat. Nos. B14,655,771 and B14,733,665.

All documents cited herein, including the foregoing, are incorporated herein by reference in their entireties for all purposes.

SUMMARY OF THE INVENTION

Accordingly, there is a need for ultrasonic dilatation catheters capable of dilating stents and arteries using relatively lower pressure than conventional dilatation systems. It is relatively low pressure ultrasonic assisted balloon stent expansion and balloon angioplasty to which this invention relates. Ultrasonic assisted balloon angioplasty may include using a relatively lower inflation pressure to dilate an ultrasonically relaxed body vessel.

One embodiment of the invention is a balloon catheter including an ultrasound energy delivery probe or wire situated between the balloon and a stent in a body lumen. In use, the balloon may be inflated to a bias pressure near, but below, that pressure needed to cause stent expansion. Thereafter, the ultrasound may be turned on to cause the stent to expand. For a Palmaz-Schatz coronary artery stent, U.S. Pat. No. 4,733,665, the bias pressure is typically about 2 atm. The invention may also be used with a Wallstent® Endoprothesis Device such as U.S. Pat. No. 4,655,771. In use, the balloon bias pressure creates a bias stress in the stent. Thereafter, the ultrasound causes the stent to vibrate, and periodically causes a strain in the hoop direction. The ultrasound also may cause the arterial walls to relax. See Derek R. Boughner and Margot R. Roach, *Effect of Low Frequency Vibration on the Arterial Wall*, CIRCULATION RESEARCH, August 1971, at 136. The ultrasound causes the stent to vibrate, and periodically causes a strain in the hoop direction. The ultrasonically induced strain causes the metal of the stent to pass its yield point, and deformation occurs in the hoop direction, in the circumferential direction, causing the stent to radially expand. The deformation cycle may be repeated with continued delivery of ultrasonic cycles and balloon bias pressure to the stent for further radial expansion. The bias balloon pressure may be increased as the stent becomes work-hardened. The balloon pressure and acoustical energy may be applied simultaneously or prior to the other to the stent. Other embodiments and methods of use of the invention are described below.

Transducers known in the art may be optimized to produce linear probe displacement in coronary arteries for thrombolysis. Devices known in the art include U.S. Pat. Nos. 5,163,421; 5,269,291; 5,269,297; 5,380,373; 5,427,118; 5,447,509; 5,451,220; 5,474,530; 5,524,620; and 5,611,807. Other ultrasound delivery probes are also known in the art.

The transducer in the present invention may be a separate component or integrally designed into the catheter. The device may include an acoustic horn integrally designed into the catheter. The horn may be approximately 3 feet long, welded to three fine titanium wires or other materials known in the art to form a stem. The wires or delivery probes may be disposed at or near the balloon for stimulation of the stent. The cardiologist may advantageously use a system including a comparatively short balloon and a footswitch or button activated ultrasound energy generator system and selectively expand portions of the stent to desired arterial dimensions in an efficient and reliable way as compared to high pressure balloon dilatation.

Another advantage of ultrasonic energy vibrations during stent dilatation or angioplasty is that arterial relaxation may occur during or following ultrasonic energy delivery to the coronary artery. This relaxation may reduce the pressure required to expand the stent by reducing the pressure required to dilate the arterial wall. Additionally, the high frequency oscillating energy may facilitate stent expansion by allowing the stent to move through the plaque.

It is advantageous for the acoustical energy generator to cause a standing wave in the stent and body vessel system. Electromagnetic systems may easily deliver the required energy for a standing wave. Alternatively, ultrasound stimulation may efficiently create an acoustical standing wave and may provide the greatest amount of stent expansion. A preferred balloon inflation pressure ranges from about 4 atm to about 6 atm and acoustical energy delivery at a range from about 20 kHz to about 40 kHz at the stent.

In sum, the invention relates to an ultrasonic balloon catheter and stent assembly including a balloon catheter. The balloon catheter has a shaft with proximal and distal portions and one or more lumens. The balloon is connected to the distal portion of the shaft and is in communication with an inflation lumen. The balloon has an uninflated and an inflated state. An acoustical energy generator is associated with the catheter and is adapted to provide oscillating energy at or near the balloon. A stent for placement in a body lumen is included and sized and configured to allow the balloon to be inserted in the stent in the uninflated state wherein transmission of the oscillating energy to the stent in combination or alternating with balloon pressure to a predetermined pressure causes deformation of the stent. The acoustical energy generator may be an ultrasound transducer or horn and adapted to communicate energy through at least one wire to at or near the stent. The acoustical energy generator may be a mechanical mechanism and adapted to communicate energy to at or near the stent. The acoustical energy generator may be an ultrasound transducer disposed on or about the catheter or balloon and adapted to communicate ultrasonic energy to at or near the stent. The acoustical energy generator may be controlled from outside the body. The acoustical energy generator may be operated by a power source selected from the group consisting of battery, magnet, and electricity. The required inflation pressure of the balloon to expand a stent may be less than about 12 atm. The acoustical energy generator may be adapted to increase the stress and strain on a stent. The acoustical energy and balloon pressure in combination or alternatingly may be adapted to at least partially expand at least one of a body vessel or stent. One of the acoustical energy or balloon pressure may be applied to the stent before the other and may be adapted to at least partially strain at least one of a body vessel or stent. The balloon may be adapted to at least partially expand at least one of a body vessel or stent at a pressure range of about 2 atm to about 7 atm while simultaneously applying the acoustical energy at or near the balloon at a range of about 20 kHz to about 40 kHz.

The invention also relates to an ultrasonic balloon catheter and stent assembly including a balloon catheter having a shaft with proximal and distal portions and one or more lumens. A balloon is connected to the distal portion of the shaft and is in communication with an inflation lumen. The balloon has an uninflated and an inflated state. An acoustical energy generator is adapted to provide acoustical energy at or near the balloon. A stent for placement in a body lumen is included and sized and configured to allow the balloon to be inserted in the stent in the uninflated state wherein transmission of the oscillating energy to the stent at a range of about 10 kHz to about 50 kHz in combination with balloon pressure at a pressure range of about 2 arm to about 6 atm causes deformation of the stent. The balloon may be adapted to at least partially expand at least one of a body vessel or stent at a pressure range of about 2 arm to about 6 arm while simultaneously applying the acoustical energy at or near the balloon at a range of about 20 kHz to about 40 kHz. The balloon may be adapted to at least partially expand at least one of a body vessel or stent at a pressure range of about 4 arm to about 6 arm while simultaneously applying the acoustical energy at or near the balloon at a range of about 25 kHz to about 35 kHz.

The invention also relates to a method of expanding a stent including the steps of inserting the stent in a body vessel, disposing a catheter at or near a stent, the catheter having a balloon associated with a acoustical or ultrasonic energy generator, and transmitting acoustical or ultrasonic energy generated from the acoustical energy generator to the stent and simultaneously applying a predetermined pressure to the balloon to thereby expand the stent. The predetermined pressure may range from about 2 arm to about 6 arm and the energy may be in the range from about 10 kHz to 50 kHz. The predetermined balloon pressure may be increased upon work-hardening of the stent. The energy generated from the acoustical energy generator may be intermittently transmitted to a location at or near the stent.

The invention also relates to a method of expanding a stent including delivering a stent to a treatment site, the stent having an interior surface, delivering a balloon catheter to the treatment site, the balloon catheter having a tubular shaft defining a lumen, the catheter having a proximal portion and a distal portion, a balloon mounted on the catheter distal portion and in communication with the lumen, and an acoustical energy generator adapted for transmitting acoustical energy to at or near the balloon and to strain the stent in its hoop direction causing expansion of the stent, disposing the balloon within the stent and transmitting acoustical energy to at or near the stent at a predetermined location and inflating the balloon to a predetermined pressure thereby applying force and energy to the stent interior surface or stent hoop direction. The balloon pressure force and ultrasonic energy may be simultaneously transmitted to the stent. The balloon pressure and ultrasonic energy may be alternatingly transmitted to the stent. The acoustical energy may be intermittently transmitted at a predetermined location of the stent.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 1 is a side view of a transducer system having three leads proximal of and incorporated into the balloon catheter of FIG. 1A;

FIG. 2 is an end view of the balloon catheter of FIG. 1A along the line 2–2;

FIG. 5 is a side view of an alternative embodiment of the present invention incorporating a mechanical device at or near the balloon.

DETAILED DESCRIPTION OF THE INVENTION

Figure 3:
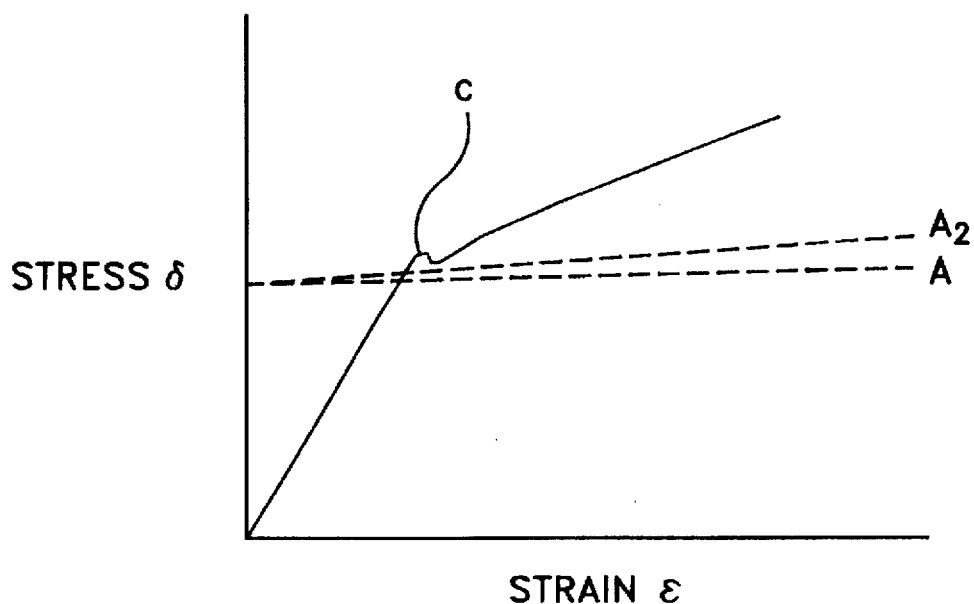
FIG. 3 is a graph illustrating stress versus strain on a stent using the present invention.

Reference is made to FIGS. 1 and 2 which illustrate a catheter 10 having ultrasonic wires 13 disposed between the exterior of the balloon 15 and a stent 18.

The catheter 10 comprises a tubular shaft 14 having proximal and distal portions 3 and 4 respectively and a balloon 15. The dilatation balloon 15 is mounted on the distal portion 4 of shaft 14, e.g., for expanding an expandable stent 18. An inflation lumen 7 extends throughout the shaft 14 and is fed by a pressure source 19 for inflating the balloon 15. The pressure source 19 is connected to the inflation lumen 7 and communicates with the balloon 15. The transducer 11 is connected to a power source 22 and a horn 12. The horn 12 may be an integral part of the catheter 10 or be located proximal of the catheter 10. The horn 12 is connected to ultrasonic wires 13 extruded in the wall of the shaft 14, or the wires 13 may run in a channel or loosely in a lumen in the shaft 14 of the catheter 10. The wires 13 may form a stem and exit through the wall of the shaft 14 proximal of the balloon 15 and be equidistantly disposed on the balloon 15. An alternative embodiment may have the wires 13 disposed inside the balloon 15. Three ultrasonic wires 13 are illustrated in FIGS. 1–2, however, one or more ultrasonic wires 13 may be incorporated. The ultrasonic wires 13 are preferably spaced equidistantly apart and disposed adjacent to the balloon 15 and under the stent 18. Additional embodiments of the invention are included below.

A third device includes a miniature ultrasonic transducer 25 (not illustrated), optimized to expand a stent 18, disposed on the distal portion 4 of a catheter 10 at or near the balloon 15 for stimulation of the stent 18. U.S. Pat. No. 5,269,291 describes a miniature ultrasonic transducer.

FIG. 3 illustrates stress versus strain on a stent 18 using the present invention. Referring to FIG. 1, as the balloon 15 is inflated to a pressure near, but below, that pressure needed to cause stent 18 expansion, the ultrasound from the transducer 11 and horn 12 may be turned on to cause the stent 18 to expand. The balloon 15 pressure from the pressure source 19 creates a bias stress in the stent 18 which is illustrated by dotted line A or A2 in FIG. 3. The ultrasound causes the stent 18 to vibrate, and periodically causes a strain in the hoop direction. The ultrasonically induced strain and oscillating energy in combination with balloon bias pressure causes the metal of the stent 18 to pass its yield point at point C, and deformation of the stent 18 occurs causing the stent 18 to become larger. The deformation cycle of the stent 18 may be repeated with continued delivery of ultrasonic cycles to the stent 18. Alternatively, the ultrasound may be turned on prior to inflation of the balloon 15. The balloon pressure may be elevated as the stent 18 becomes work-hardened from the ultrasound or acoustical energy. This increase in balloon bias pressure is illustrated as dotted line A2. Other variations of balloon bias pressure A, A2 in combination with the ultrasonic energy from the transducer 11 and horn 12 are also possible.

Figure 4:
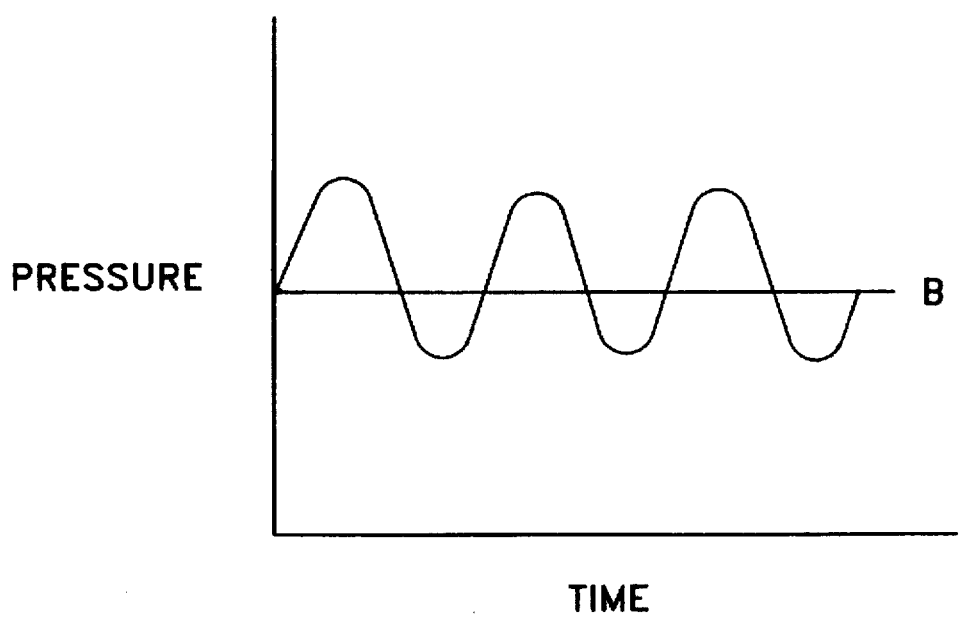
FIG. 4 is a graph illustrating pressure versus time on a stent using the present invention.

FIG. 4 illustrates pressure versus time on a stent 18 using the present invention. The amplitude and frequency of the pressure and ultrasonic energy may vary depending on the pressure source 19 and design of the stent 18. Bias is created by the balloon pressure and is illustrated by the line B. Variations of balloon bias pressure and frequency of the ultrasonic energy are also possible.

A fourth device includes a series of bent wires, or a ball on a wire which may be rotated to produce the desired result. FIG. 5 illustrates a mechanical device 30 such as a ball or wire adapted to rotate or slide in a balloon 15 to create an oscillating energy source at the stent 18. The proximal end of the ball or wire 30 is connected to a mechanism 32 such as a motor and a power source 22. Axial displacement of the wire 30 may advantageously deliver pressure surges and energy to the adjacent stent 18 for relatively low pressure inflation of the stent 18. A pressure source 19 is connected to the inflation lumen 7 in the shaft 14 and communicates with the balloon 15.

The balloon inflation pressure and acoustical energy necessary to expand a stent 18 will be influenced by the design and type of stent 18 used.

It will be evident from considerations of the foregoing that the pressure assisted ultrasonic dilatation catheter and methods of use are now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. An ultrasonic balloon catheter and stent assembly comprising:
    a balloon catheter having a shaft with proximal and distal portions and one or more lumens, a balloon connected to the distal portion of the shaft and in communication with an inflation lumen, the balloon having an uninflated and an inflated state;
    an acoustical energy generator associated with the catheter and adapted to provide oscillating energy at or near the balloon; and
    a stent for placement in a body lumen and sized and configured to allow the balloon to be inserted in the stent in the uninflated state, wherein the acoustical energy generator transmits oscillating energy to the stent whereby transmission of the oscillating energy to the stent in combination or alternating with balloon pressure to a predetermined pressure causes deformation of the stent.

2. The ultrasonic balloon catheter and stent assembly of claim 1 wherein the acoustical energy generator is an ultrasound transducer and adapted to communicate energy through at least one wire to at or near the stent.

3. The ultrasonic balloon catheter and stent assembly of claim 1 wherein the acoustical energy generator is a mechanical mechanism and adapted to communicate energy to at or near the stent.

4. The ultrasonic balloon catheter and stent assembly of claim 1 wherein the acoustical energy generator is an ultrasound transducer disposed on or about the catheter or balloon and adapted to communicate ultrasonic energy to at or near the stent.

5. The ultrasonic balloon catheter and stent assembly of claim 1 wherein the acoustical energy generator is controlled from outside the body.

6. The ultrasonic balloon catheter and stent assembly of claim 1 wherein the acoustical energy generator is operated by a power source selected from the group consisting of battery, magnet, and electricity.

7. The ultrasonic balloon catheter and stent assembly of claim 1 wherein the required inflation pressure of the balloon to expand a stent is less than about 12 atm.

8. The ultrasonic balloon catheter and stent assembly of claim 1 wherein the acoustical energy generator is adapted to increase the stress and strain on a stent.

9. The ultrasonic balloon catheter and stent assembly of claim 1 wherein the acoustical energy and balloon pressure in combination or alternatingly are adapted to at least partially expand at least one of a body vessel or stent.

10. The ultrasonic balloon catheter and stent assembly of claim 1 wherein one of the acoustical energy or balloon pressure is applied to the stent before the other and is adapted to at least partially strain at least one of a body vessel or stent.

11. The ultrasonic balloon catheter and stent assembly of claim 1 whereby the balloon is adapted to at least partially expand at least one of a body vessel or stent at a pressure range of about 2 atm to about 7 atm while simultaneously applying the acoustical energy at or near the balloon at a range of about 20 kHz to about 40 kHz.

12. An ultrasonic balloon catheter and stent assembly comprising:

a balloon catheter having a shaft with proximal and distal portions and one or more lumens, a balloon connected to the distal portion of the shaft and in communication with an inflation lumen, the balloon having an uninflated and an inflated state;

an acoustical energy generator adapted to provide acoustical energy at or near the balloon;

a stent for placement in a body lumen and sized and configured to allow the balloon to be inserted in the stent in the uninflated state whereby transmission of the oscillating energy to the stent at a range of about 10 kHz to about 50 kHz in combination with balloon pressure at a pressure range of about 2 atm to about 6 atm causes deformation of the stent.

13. The ultrasonic balloon catheter and stent assembly of claim 12 whereby the balloon is adapted to at least partially expand at least one of a body vessel or stent at a pressure range of about 2 atm to about 6 atm while simultaneously applying the acoustical energy at or near the balloon at a range of about 20 kHz to about 40 kHz.

14. The ultrasonic balloon catheter and stent assembly of claim 12 whereby the balloon is adapted to at least partially expand at least one of a body vessel or stent at a pressure range of about 4 atm to about 6 atm to while simultaneously applying the acoustical energy at or near the balloon at a range of about 25 kHz to about 35 kHz.

15. A method of expanding a stent comprising the steps of:

inserting the stent in a body vessel;

disposing a catheter at or near a stent, the catheter having a balloon associated with an acoustical or ultrasonic energy generator; and transmitting acoustical or ultrasonic energy generated from the acoustical energy generator to the stent and simultaneously applying a predetermined pressure to the balloon to thereby expand the stent.

16. The method of expanding a stent of claim 15 wherein the predetermined pressure ranges from about 2 atm to about 6 atm and the energy is in the range from about 10 kHz to 50 kHz.

17. The method of expanding a stent of claim 15 wherein the predetermined balloon pressure increases upon work hardening of the stent.

18. The method of expanding a stent of claim 15 wherein the energy generated from the acoustical energy generator is intermittently transmitted to a location at or near the stent.

19. A method of expanding a stent comprising delivering a stent to a treatment site, the stent having an interior surface;

delivering a balloon catheter to the treatment site, the balloon catheter having a tubular shaft defining a lumen, the catheter having a proximal portion and a distal portion, a balloon mounted on the catheter distal portion and in communication with the lumen, and an acoustical energy generator adapted for transmitting acoustical energy to at or near the balloon and to strain the stent in its hoop direction causing expansion of the stent;

disposing the balloon within the stent; and transmitting acoustical energy to at or near the stent at a predetermined location and inflating the balloon to a predetermined pressure thereby applying force and energy to the stent interior surface or stent hoop direction.

20. The method of expanding a stent of claim 19 wherein the balloon pressure and ultrasonic energy are simultaneously transmitted to the stent.

21. The method of expanding a stent of claim 19 wherein the balloon pressure and ultrasonic energy are alternatingly transmitted to the stent.

22. The method of expanding a stent of claim 19 wherein acoustical energy is intermittently transmitted at a predetermined location of the stent.

* * * * *